United States Patent [19]

Perazzo

[11] Patent Number: 5,269,454
[45] Date of Patent: Dec. 14, 1993

[54] DISPOSABLE CONTAINER FOR BIOHAZARDOUS MEDICAL WASTE

[75] Inventor: John R. Perazzo, Cincinnati, Ohio

[73] Assignee: Fibretainer, Incorporated, Cincinnati, Ohio

[21] Appl. No.: 975,669

[22] Filed: Nov. 13, 1992

[51] Int. Cl.⁵ .................... B65D 21/02; B65D 5/12; B65D 1/42

[52] U.S. Cl. ................ 229/4.5; 229/915; 229/125.28; 206/363; 206/366; 206/503

[58] Field of Search .............. 229/4.5, 915, 125.28; 206/363, 366, 503

[56] References Cited

U.S. PATENT DOCUMENTS

| | | | |
|---|---|---|---|
| 904,095 | 11/1908 | Shea | 229/4.5 |
| 1,627,042 | 5/1927 | Mason et al. | 229/4.5 |
| 3,820,685 | 6/1974 | Reisman | 229/4.5 |
| 5,046,660 | 9/1991 | Magnoni | 229/4.5 |

*Primary Examiner*—William I. Price
*Attorney, Agent, or Firm*—Wood, Herron & Evans

[57] ABSTRACT

A disposable container for biohazardous medical waste comprising a cylindrical, tapered body having a circular bottom attached on one end and a circular lid secured in place on an opposite end by interlocking tabs and slots. Located above the lid are handles formed integrally with the body of the container for use in transporting the container without contacting the medical waste contained therein. The lid is secured in place and cannot be deliberately or accidentally removed without damaging the container. The bottom, body, and lid of the container are constructed of solid fiber paperboard which is both leak and puncture resistant and readily flammable for efficient incineration. The tapered geometry of the body permits easy stacking of the containers thereby requiring a minimal amount of storage space.

3 Claims, 1 Drawing Sheet

DISPOSABLE CONTAINER FOR BIOHAZARDOUS MEDICAL WASTE

BACKGROUND OF THE INVENTION

This invention relates to a disposable container for waste, and more particularly, to a container which is both puncture and leak resistant and can be efficiently incinerated for disposal of biohazardous medical waste.

In the disposal of biohazardous medical waste, containers such as corrugated paperboard boxes, plastic containers, and other readily available receptacles have been used. The concern over disposal of biohazardous medical waste has recently increased and a need has developed for an appropriate disposal container. Typically, the containers used for disposal of biohazardous medical waste are designed either for all-purpose storage uses or disposing of general non-hazardous refuse. The disposal of biohazardous medical waste presents unique problems for safety, identification, and cost efficiency which are not required when discarding standard refuse.

Medical waste commonly includes discarded syringes, needles, and other sharp objects which can puncture or penetrate common corrugated paper boxes or plastic containers. The dangers present from such a puncture of the disposal container is not limited to the fact that the disposal container or vessel could rupture and thereby discharge the medical waste container therein. In addition, handlers of the biohazardous medical waste containers are exposed to the risk of injury and infection from contact with such unsterile items.

Even puncture resistant containers in use today present risks for the handling of biohazardous medical waste. The boxes now used often have openings as handles in their sides making it necessary for the handler to insert a hand into the box in order to lift it and thereby possibly contacting the waste. Alternatively, the box can be lifted from the bottom while supporting it against the handler's body which further raises the risk of injury from a needle or sharp object which protrudes through the side or bottom of the box.

Biohazardous medical waste often consists of not only solid objects but also liquid waste which are discarded into a common container. Therefore, the disposal container should be leak proof in addition to puncture resistant. Common corrugated paperboard boxes often have flap folds on the bottom which must be taped to provide a leak resistant closure or lined with plastic bags to prevent escape of the liquid waste. In addition, corrugated paperboard boxes often also close on top by folding flaps in combination with taping the container closed. This technique does not afford safe closure or leak resistant containment of the biohazardous medical waste.

Once in the container, biohazardous medical waste is commonly burned in high efficiency incinerators currently in use for the disposal of biohazardous waste. Corrugated paperboard boxes including layers of tape or plastic bags are either flame resistant or burn very inefficiently when disposed of in such a way.

No container commercially available today exists which is capable of being easily assembled and conveniently stored for the safe and efficient disposal of biohazardous medical waste. Furthermore, containers currently in use are generic and commonplace which do not afford an indication that the contents are biohazardous medical waste requiring special treatment and handling. Standard containers merely imprinted with the biohazardous symbol are not readily identifiable in that they are commonly used for non-waste disposal purposes and are not afforded the recognition required for hazardous waste.

SUMMARY OF THE INVENTION

The present invention encompasses a puncture and leak resistant container for biohazardous medical waste which is readily identifiable as such and can be easily secured closed without the benefit of tape or adhesives. In addition, a container of the present invention can be safely handled without risking injury by contacting the hazardous waste contained thereon. The full container can also be efficiently stacked, stored and incinerated as required. The present invention combines these features in a cost efficient, readily identifiable, and easily usable biohazardous medical waste disposable container.

This invention is a disposable container which has a generally cylindrical and tapered body. The container is sealed on one end by a circular bottom attached to the body and a generally circular lid on an opposite end. The lid is of greater diameter than the bottom and can be secured to the filled container with a number of tabs around its circumference which lock the lid in place when they are inserted through a number of slots contained in the body of the container. The slots are located just below handles which are formed into the body of the container and have openings for grasping the container. The handles and openings are advantageously located above the lid to avoid user contact with the medical waste in the container. When in place, the lid is secure and cannot be easily removed, accidently or deliberately, without damaging the container.

A cavity is formed by the lid and the handles which projects above the lid from the body of the container. This cavity is adapted to receive the bottom of a second container according to the invention in that the diameter of the bottom is less than the diameter of the lid due to the body's tapered geometry. In this way the container filled with biohazardous medical can be easily stored in a minimum amount of space until such time that it is disposed of or incinerated.

BRIEF DESCRIPTION OF THE DRAWINGS

The objectives and features of the invention will become more readily apparent from the following detailed description taken in conjunction with the accompanying drawings in which.

DETAILED DESCRIPTION OF THE INVENTION

Figure 1:
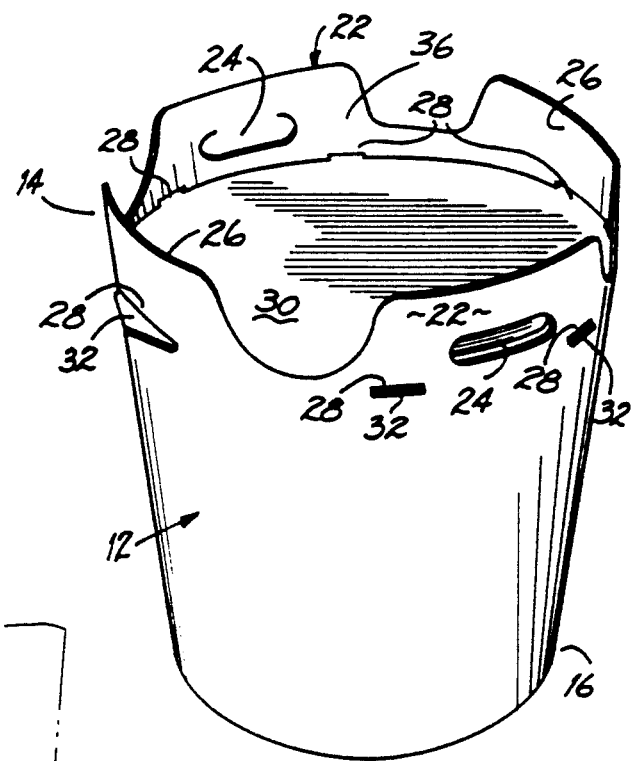
FIG. 1 is a perspective view of a disposable container of the present invention.
Figures 2, 3:
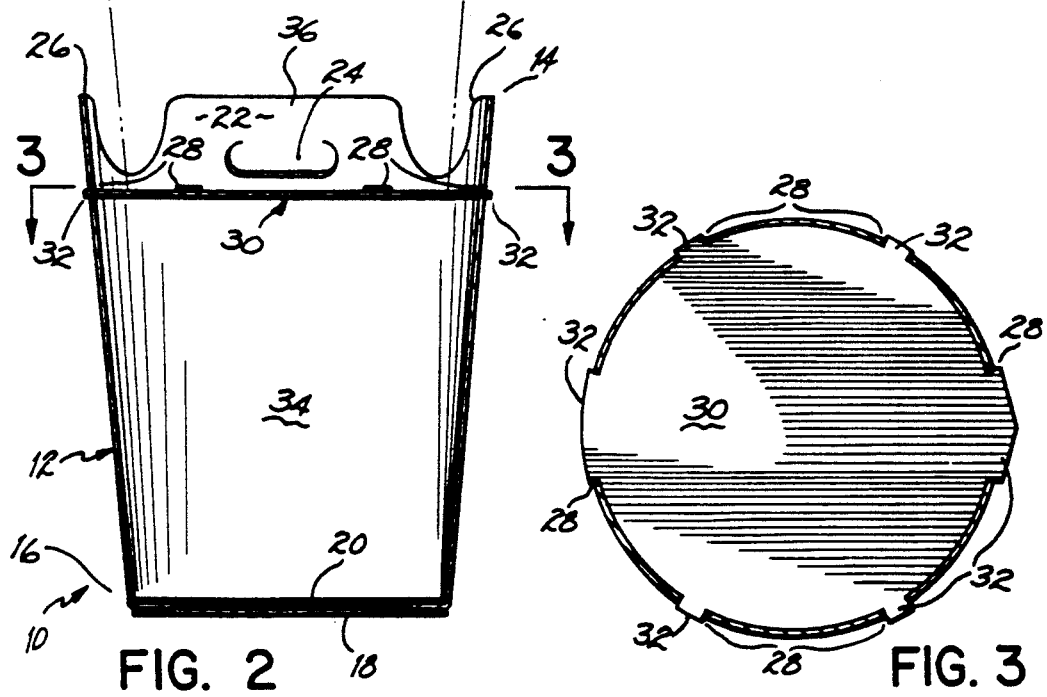
FIG. 2 is an axial cross-sectional view of a container of the present invention with the lid secured in place showing in phantom lines a second container of the present invention stacked on top thereof.
FIG. 3 is a cross-sectional view taken along line 3—3 of FIG. 2 of the disposable container of the present invention with the lid in place.

Referring to FIG. 1, a disposable container 10 for biohazardous medical waste according to the present invention is shown. The container has a tapered, cylindrical body 12 constructed of solid fiber paperboard which is both leak proof and puncture resistance to sharp objects such as needles and syringes. The taper of the body 12 provides for a greater diameter top end 14 than bottom end 16 of the container. The container 10 of the present invention includes a bottom 18 secured to the body as shown in FIG. 2. In a preferred embodiment of the present invention, an inner bottom 20 is provided just above the bottom 18. This double layered bottom configuration of the present invention ensures increased leak resistance and enhanced strength to support the weight of the waste in the container 10.

Handles 22 are integrally formed with the body 12 of the container and project from the top end 14 of the body. The handles include openings 24 through which the container 10 can be grasped and lifted. Flaps 26 also project from the top end 14 and are positioned with the handles 22 around the perimeter of the container. The function of the flaps 26 is to enhance the ability to stack containers 10 of the present invention as detailed later in the disclosure.

In the preferred embodiment of the present invention, slots 28 are provided in the body 12 of the container just below the handles 22 and flaps 26 as shown in FIG. 1. The slots 28 are designed to secure a lid 30 onto the container 10. The slots 28 receive tabs 32 which project from the circumference of the lid 30 as shown in FIG. 3. When in place, the lid 30 is positioned below the handles 22 and flaps 26 defining a containment volume 34 with the body 12 and bottom 18 of the container for the biohazardous medical waste. The handles 22 and openings 24 are located external to and above the containment volume 34 thereby preventing the handler of the container 10 from contacting medical waste contained therein.

The lid 30 is easily guided into position due to the tapered geometry of the body 12. The tabs 32 around the perimeter of the lid 30 are inserted into slots 28 in the body 12 of the container and the interlocking relationship between the slots 28 and the tabs 32 secures the lid 30 just below the handles 22. Once in place, the lid 30 is not easily removed either deliberately or accidently without damaging the container 10 or the lid 30 itself.

The combination of the tapered geometry of the body 12 and the interlocking relationship between the lid 30 and the body 12 allows containers 10 of the present invention to be conveniently stacked and stored in a space efficient manner. The lid 30, handles 22, and flaps 26 define a cavity 36 into which the bottom of a second container 38 of the present invention can be placed thereby stacking the containers. The diameter of the bottom 18 is less than the diameter of the lid 30 thereby enabling the stacked configuration shown in FIG. 2 where the second container 38 is shown in phantom on top of a container 10 of the present invention.

The container 10 of the present invention comprising the bottom 18, body 12, and lid 30 of the preferred embodiment is constructed of a solid fiber paperboard material. This material affords resistance to puncture by needles or other sharp objects that is far superior to corrugated paperboard. The solid fiber paperboard also burns more efficiently in the incinerators being used in the disposal of biohazardous medical waste than corrugated paperboard or plastic materials.

From the above disclosure of the general principles of the present invention and the preceding detailed description of a preferred embodiments, those skilled in the art will readily comprehend the various modifications to which the present invention is susceptible. Therefore, we desire to be limited only by the scope of the following claims and equivalents thereof:

We claim:

1. A disposable container for biohazardous medical waste comprising:
   a tapered generally cylindrical body constructed of puncture resistant flammable solid fiber paperboard, said body having a top end and an opposing bottom end, said top end having a greater diameter than said bottom end;
   a generally circular bottom constructed of puncture resistant flammable solid fiber paperboard attached to said bottom end to form a leak resistant bottom seal with said body;
   a plurality of handles extending from and integrally formed with said body at said top end, each said handle having an opening formed therein for convenient handling of the container;
   a plurality of slots in said body located between said bottom and said handles; and
   a generally circular lid constructed of puncture resistant flammable solid fiber paperboard, said lid having a plurality of tabs extending from the circumference thereof, said tabs mating with said slots to interlock said lid and said cylindrical body such that said lid is only removable upon damaging the container, said lid along with said bottom and said body defining a containment volume for biohazardous medical waste container therein, said slots being located on said body below said handles such that a person using said handles avoids contact with the biohazardous medical waste in said containment volume.

2. A container of claim 1 wherein said bottom is a double bottom having an inner bottom and an outer bottom for increased strength and resistance to leaks and punctures.

3. A container of claim 1 wherein a cavity is formed by said lid and said handles when said lid is secured to said body with said tabs and said slots such that a second container can be stacked on said first container by resting a bottom of said second container on said lid of said first container.

* * * * *